United States Patent [19]

Beck

[11] 4,324,782

[45] Apr. 13, 1982

[54] **DENTAL CARIES INHIBITING PRODUCT OF IMMUNIZED COW'S MILK HAVING ANTIBODIES SPECIFIC TO KILLED *STREPTOCOCCUS MUTANS* CELLS**

[76] Inventor: Lee R. Beck, 2550 Dunmore Pl., Birmingham, Ala. 35226

[21] Appl. No.: 776,249

[22] Filed: Mar. 10, 1977

Related U.S. Application Data

[63] Continuation-in-part of Ser. No. 436,946, Jan. 28, 1974, abandoned.

[51] Int. Cl.$^3$ .............................................. A61K 39/09
[52] U.S. Cl. ...................................................... 424/87
[58] Field of Search ................................... 424/48–58, 424/85–87

[56] References Cited

U.S. PATENT DOCUMENTS 3,128,230  4/1964  Heinbach ............................. 424/87
3,376,198  4/1968  Petersen et al. ...................... 424/85

FOREIGN PATENT DOCUMENTS 1810438  7/1969  Fed. Rep. of Germany ........ 424/86
2522999  12/1976  Fed. Rep. of Germany .
2313076  12/1976  France .
1211876  11/1970  United Kingdom .

OTHER PUBLICATIONS

Berkenbilt et al., J.A.D.A. vol. 83: 332–337, Aug. 1971, Development of Antibodies to Cariogenic Streptococci in Children.
Olson et al., Chem. Abstracts vol. 77 #36969 (1972) of Infer. Immunity S(4):419–427 (1972) Adherence Inhibition of *Streptococcus mutans*. Assay Reflecting a Possible Role of Antibodies in Dental Caries Prophylaxis, Exhibit "A".
Bowen, British Dental Journal: 159–160, Feb. 18, 1969, A Vaccine Against Dental Caries (Exhibit C).
Taubman (1973), Symposium on Comparative Immunology of the Oral Cavity, Phila., Pa. (1971) DHEW Pub. No. NIH73–438: 138–158, "Role of Immunization in Dental Disease".
McGhee et al., Immunochemistry 12: 817–823 (1975) Rat Immunoglobulins in Serum and Secretions: Purification of Rat IgM, IgA and IgG and their Quantitation in Serum, Colostrum, Milk and Saliva.
McGhee et al., J. Immunology 114 No. 1 Part Z: 303–305, Jan. 1975, Effective Immunity to Dental Caries: Protection of Gnotobiotic Rats by Local Immunization with *Streptococcus mutans*.
Michalek et al., Science 192:1238–1240, Jun. 18, 1976, Ingestion of *Streptococcus mutans* Induces Secretory Immunoglobulin A and Caries Immunity.

*Primary Examiner*—Shep K. Rose
*Attorney, Agent, or Firm*—Frost & Jacobs

[57] ABSTRACT

The use of a milk product containing antibodies to *Streptococcus mutans* for ingestion through the oral cavity and/or application to teeth to inhibit or reduce the incidence of dental caries, and the product itself.

7 Claims, No Drawings

DENTAL CARIES INHIBITING PRODUCT OF IMMUNIZED COW'S MILK HAVING ANTIBODIES SPECIFIC TO KILLED *STREPTOCOCCUS MUTANS* CELLS

CROSS-REFERENCE TO RELATED APPLICATION

This application is a continuation-in-part of U.S. Patent Application Ser. No. 436,946, filed Jan. 28, 1974, now abandoned.

BACKGROUND OF THE INVENTION

Studies have indicated that tooth decay is a natural consequence of the presence of oral bacteria (*Streptococcus mutans*). Specifically, it is known that bacteria *S. mutans* attach to the enamel surface of the tooth and, under the proper circumstances of temperature, acidity and availability of substrate, a colonization process takes place—the bacteria colony in turn creates the actual caries formation in the tooth enamel and then into the tooth structure.

Generally, it is known to immunologists that contacting a bacteria with an antibody for that bacteria, will inhibit the growth of the bacterial colony. *Streptococcus mutans* is present in the mouth of most human beings and it is only the level or the degree of natural resistance to this bacteria which is different in each oral cavity. Set with the conducive environmental elements, the colonization progresses at a rapid rate.

The literature reports several attempts at controlling the incidence of dental caries in a living oral cavity by active immunization, i.e. by either systemic injection or topical application of antigen in the hope of producing an effective antibody titer in said oral cavity. The results have been mixed both from the standpoint of therapeutic effect for controlling caries and the incidence of undesirable side reactions. Though the knowledge that *Streptococcus mutans* is the principal actor in the formation of dental caries, has been in the literature for some 40 years, there was not available prior to this invention an acceptable immunological system that achieves the desired result dentally, yet avoids the hazards inherent in any system of active immunization. Put succinctly, researchers in the field did not see the possibilities in utilizing a passive immunization system, wherein the antibodies for *Streptococcus mutans* are developed exogenously and ingested through and/or applied to the oral cavity of the host animal.

BRIEF SUMMARY OF THE INVENTION

The invention resides in the discovery that dental caries may be controlled, and thus the incidence of caries reduced, by a passive immunization process that utilizes a bovine-milk generated source of antibodies to *Streptococcus mutans*. No claim is made to the broad idea that domestic animals can be used to generate antibodies to injected antigens.

It is generally accepted that the immunological functions of the oral cavity are controlled by IgA antibodies and not IgG or the other established classes of immunoglobulin.

Surprisingly, it was found that an exogenous milk source of immunoglobulin comprised principally of IgG, namely, bovine milk, is an effective source of antibody for controlling the incidence of dental caries. Equally surprising is that the relatively brief residual time of the bovine milk generated antibody and the poor adhesive characteristic of the principal immunoglobulin of bovine milk, namely IgG, will permit such an efficaceous result with a passive immunization process.

That bovine milk antibody for *S. mutans* is therapeutically effective carries with it the added advantage that this product, or concentrations thereof, is a nutritious, compatible product that is almost universally tolerable by the human species. Moreover, being an exogenous source of antibody, it is conveniently susceptible to simple, controlled testing for side effects and removal of the causative agents, a recourse not available to a system utilizing active immunization.

Although the cow is the principal commercial milk producer in most parts of the world, other bovine milk producing species would be a suitable source for generating the milk immunoglobulin of this invention. For example, a suitable bovine species is the goat.

For purposes of further describing this invention the specification will hereafter concern itself with production of *S. mutans* antibody utilizing a cow as the exogenous source.

DESCRIPTION OF THE PREFERRED EMBODIMENT

The exact technique for immunizing a cow in order to produce a specific antibody is known in the veterinary field. Generally, the cows are immunized in two stages. The first stage involving four injections given intramuscularly at weekly intervals. The second stage of immunization comprises intramuscular injections given to the cows at 15 day intervals. A novel claim in the actual immunization technique is not being made. Actually, a strain of *Streptococcus mutans* was taken and cultured in accordance with established techniques. A cow was then immunized in accordance with the established techniques to generate a milk product. Following immunization, blood samples of the cow are taken until the serum antibody titer reaches its highest level, then the milk is collected. The milk itself was then dried and powdered, again in accordance with established techniques to produce a powdered milk containing antibodies to the *Streptococcus mutans*. Actually, a bovine milk immunoglobulin was produced. This product then becomes the basic ingredient of any one of several consumer products, for example, a. The dried milk itself can be diluted to form a mouthwash. The mouthwash would be effective simply by being rinsed through the mouth on a daily basis, thereby inhibiting the colonization of the *Streptococcus mutans* on the enamel surface of the tooth. It should be understood that the *S. mutans* antibodies may be isolated from the milk and used as the active component with a number of other carriers. Hereafter reference to bovine milk generated antibodies shall mean the antibodies in association with the natural milk, whole or concentrated, or any other concentrated form of the antibodies, including without limitation, the isolation of the *S. mutans* antibody.

b. The product could be incorporated in a sugarless confection in the form of a gum or candy, ice cream or any other food form by incorporating substantial percentages of the immunoglobulin in that product.

c. The immunoglobulin could be incorporated in standard cleansing powders or tooth pastes used by dentists or sold commercially.

d. As a matter of fact, the reconstituted milk is effective in and of itself for inhibiting colonization of the Streptococcus mutans, i.e., simply drinking the milk causes enough contact between the teeth and immunoglobulin to be effective.

Note, however, that the discovery deals primarily with the generation of the milk immunoglobulin and its use in a passive immunization system application of the milk immunoglobulin to the tooth surface. The absorption of the milk immunoglobulin into blood via the gastrointestinal tract and subsequent delivery to the oral cavity via the blood stream might be an alternative route by which the antibodies in the ingested milk could be effective against caries formation.

The desired bovine milk immunoglobulin of the present invention is preferably generated in the following way.

The S. mutans antigen used in the immunization of cows is a suspension of killed bacteria in physiological saline solution. The antigen is specifically compounded by rigorous laboratory methods and procedures to assure that the appropriate standards of identity, strength, quality, and purity are maintained.

Specimens of bacterial strains of S. mutans, such as S. mutans AHT, S. mutans BHT, S. mutans 10449 and S. mutans 6715, can be obtained from American Culture Collection which insures authenticity of the bacterial strain and the highest standard for purity that is available. Alternatively, strains can be obtained from established cultures maintained at various research institutes. Upon receipt of the desired specimens each individual bacterial strain is grown on a blood agar plate both to test the viability of the culture and to determine if the growth pattern is either typical or atypical of the bacterial strain in question. A single colony from each test culture is taken for histological examination to further insure authenticity and purity of the culture. If the culture proves pure, a single colony is used to innoculate 500 mls of standard culture broth.

All organisms are incubated as static cultures. Each culture is cultivated for 48 hours at 37° C. Following incubation, the cultures are killed by heating at 56° C. for two hours. Fresh broth is innoculated with samples of the killed bacteria and incubated for 24 hours at 37° C. to determine if the killing procedure is complete. In the event of bacterial survival, the killing procedure would be repeated until negative culture tests result. Only cultures proven sterile by this procedure are used for further processing. Sterile cultures are washed 5 times in distilled water and cells are recovered by centrifugation at $4,000 \times G$. The washed, heat-killed bacterial cells are then frozen by immersion in liquid nitrogen approximately $-90°$ C. and then freeze-dried by the process of lyophilization. The lyophilized cells are stored in sterile vials until used for the production of the S. mutans antigen.

Streptococcus mutans antigen is prepared by weighing out quantities of each of the bacterial strains desired for the antigen. For example, if a S. mutans AHT, BHT, 10449 and 6715 antigen is to be produced, one gram of heat-killed lyophilized cells of each strain would be weighed out to yield a four gram sample. The dry cells are mixed together and this mixture is suspended in 500 mls of sterile physiological saline to give a stock solution of concentrated S. mutans antigen (which, in the example given, would have a total concentration of four grams of bacteria per 500 mls of saline or 8 mg of antigen per ml of saline.) A sample from this highly concentrated solution is diluted in a serial fashion with sterile physiological saline to determine the correct dilution factor which produces an optical density reading on a spectrometer of 0.50 [unit of measure] to 0.70 percent light absorption read at a wavelength of 660 Angstroms. Previous tests have shown that this is the dilution factor necessary to give a final concentration of $2 \times 10^8$ cells per ml. The stock solution of concentrated S. mutans antigen is dispensed into multiple containers and stored frozen at 0° C. The final dilution of the concentrate is made just prior to immunization. The routine procedure is to thaw out a sufficient number of vials to immunize the number of cows to be treated. The vials are removed from freezing 24 hours prior to the planned time of immunization in order to verify sterility. The antigen concentrate is diluted at that time in its sterile container to the final concentration ($2 \times 10^8$ cells/ml) using the dilution factor previously determined. A 1 ml. sample from each container is removed with a sterile syringe and incubated in an appropriate culture broth of dialyzed triptose for 24 hours at 37° C. as a final test to assure sterility. Only sterile S. mutans antigen material is used for the immunization process. Any excess antigen remaining after the cows are innoculated is discarded.

Immune bovine milk immunoglobulin is produced by immunizing cows with the S. mutans antigen prepared as described above. The cows are injected with 5 cc of a S. mutans antigen solution having a concentration of $2 \times 10^8$ cells per ml. in the gluteus maximus muscle of a hind leg. This procedure is preferrably repeated at two week intervals beginning 3 to 4 weeks prior to the predicted day of parturition and throughout the period that the cow gives milk to produce the whole immune milk of the present invention.

Since a healthy cow is a prime requisite for safe milk, cows should all be registered cows that are free from disease as demonstrated by routine veterinary surveillance. Regular tuberculin brucellosis tests should be made and routine examinations performed on the udders and general health status of each animal. Animals exhibiting anything less than perfect health should be removed from the milk herd. These procedures insure that the immune milk is obtained only from healthy cows.

The whole immune milk produced by the immunized cows is pasteurized by heating the milk at 145° F. for 30 minutes, after which the milk temperature is lowered to 138° F. for several minutes and then cooled to a temperature of 50° F. Following pasteurization, the whole milk is further cooled to holding temperature (35° F.) and, if skimmed immune milk is desired, the fat is removed by centrifugal separation.

Following pasteurization and fat removal, the skimmed immune milk is powdered using a spray process. The spray drying system comprises a large drying chamber into which hot air 350° F. (177° C.) is blown at high velocity and the milk is atomized. Prior to atomizing, the skimmed milk is condensed by boiling in a chamber under vacuum at 100°–110° F. (38°–43° C.). A second pasteurization is done just before powdering to further reduce the probability that the dry, skimmed immune milk will contain living bacteria. The condensed skimmed milk is atomized into the chamber and the finely divided milk particles are instantaneously dried as they fall into the bottom of the tank. After the dried milk has fallen to the floor of the chamber, it is removed automatically by a mechanical device. Following removal from the chamber, the dried milk is placed in sterile containers under sanitary conditions. Each batch of powdered milk is assigned a lot number for future identification. Laboratory tests are conducted to establish the bacterial content and immunological potency of each batch of the immune milk.

In order to determine the bacterial content of the immune milk, the milk is reconstituted with distilled water to its original concentration. It should be thoroughly mixed, and sampled, with a sterile tube long enough to reach to the bottom of the mixing receptacle. Each sample should be at least 10 milliliters and should be kept in a tightly stoppered container. Closure with cotton plugs is not permitted. Samples should be iced to 4° C. and if plates are not made within 4 hours of the time when the samples were taken, the time elapsing should be reported.

A macroscopic colony count using the agar plate method is made to determine the bacterial content of the immune milk using a medium having the following composition:

|  | Percent by wt. |
| --- | --- |
| Agar (market, non oven-dried) | 1.5 |
| Beef extract | 0.3 |
| Tryptone | 0.5 |
| Glucose | 0.1 |
| Distilled water | 97.6 |

The medium is sterilized by heating to 57° C. and holding for one hour. The preferred reaction of the medium is pH 7.0, but it need not be adjusted if it is between pH 6.6 and pH 7.0. If necessary to adjust the reaction, special attention should be given to the H-ion concentration, making use of the indicator bromthymol blue. At least two dilutions with milk usually made in plating (1 to 100, 1 to 1,000 or 1 to 10,000). Each sample bottle and dilution bottle should be shaken 25 times with an up-and-down motion of about 1 foot, within an interval of 7 seconds. After dilution of the immune milk, it is added to the agar which should be poured into the plates within 20 minutes. Incubation is at 32° or 35° C. for 48 hours. The plates used for counting should have, if possible, between 30 and 300 colonies each. If there are no plates within these limits, the one having nearest to 300 colonies should be counted. Counting should be done with a lens magnifying 1½ diameters. The exact counts from each plate should be recorded, using no more than the two most significant left-hand digits in the final report. Results are expressed, not as so many "bacteria per milliliter" of milk, but as "colonies per milliliter," (or better "standard plate count per milliliter".) The practice of relying on counts from individual samples of milk to show the quality of a given supply of immune milk is not recommended, and a series of samples should be examined before rendering judgement in regard to any supply of milk.

In addition to determining the bacterial content of the immune milk by macroscopic colony count, a second determination by direct microscopic count of bacteria using the Breed method may be conducted. In this technique milk is taken in a capillary pipette, or calibrated loop, discharging 0.01 milliliter and dried over a one square centimeter area on a microscopic slide. After washing out the fat in xylene and fixing in alcohol, the film is stained in a methylene blue solution. The number of bacteria per milliliter should be estimated by counting those within a given area in a microscopic field, this area having been carefully measured and its ratio to one square centimeter determined. At least 1/10,000 part of a milliliter of milk is to be examined, and if the milk is of high grade, this must be done under favorable conditions for accurate counting. The results should be recorded as "clump microscopic count per milliliter" or "individual microscopic count per milliliter."

While the foregoing test procedures have been described using a skimmed immune milk of the present invention, a whole immune milk may be similarly tested.

The immunological activity, or potency, of the immune milk against *S. mutans* is assayed by an agglutination test in the following manner.

If the starting product is whole milk, it is centrifuged at 4,400 RPMs (approx. 2,000×G) for 15 minutes at room temperature and the skimmed milk fraction is removed for use in the testing. If the starting product is powdered milk, the powder is reconstituted in distilled water to its original concentration.

Skimmed milk prepared as described above is then processed in the following way to obtain acid whey. One milliliter of skimmed milk is added to 8.6 milliliters of distilled water and tempered to 104° F. (40° C.) for 15 minutes. The pH of this solution is then adjusted to 4.6 by the addition of 0.2 mls of a one normal solution of sodium acetate, after which the samples are cooled to room temperature and filtered through a fine grade filter paper. This technique yields a clear, acid whey having a one-to-ten dilution with respect to the original milk.

Preliminary plate agglutination tests of the acid whey can be performed by mixing 0.1 milliliters of the whey with 0.1 milliliters of appropriate *S. mutans* antigen on a clear glass plate. Agglutination is observed through a 6–10× binocular microscope after 15 minutes of incubation at room temperature. Serial threefold dilutions of the original whey fraction are made in distilled water to determine the approximate titer range.

A more precise technique may also be used—the tube agglutination method. In this method, the whey is diluted serially in distilled water. To two ml quantities of the appropriate whey dilutions, 1 to 10, 1 to 100, 1 to 1,000, 1 to 2,000, 1 to 3,000, 1 to 4,000, 1 to 5,000 1 to 10,000, and 1 to 20,000, 0.05 milliliters of a suspension of washed, whole *S. mutans* bacteria of the strain being assayed is added, and the mixture is then shaken and incubated at 98° F. (37° C.) for 18 hours before observation.

EXAMPLE 1

Cultures of *S. mutans* AHT, BHT, 10449 and 6715 were used. Each strain was grown in a dialyzed tryptose medium for 22.5 hours. The cells of each strain were harvested by centrifugation at 4,000×G and washed five times with 0.1 M phosphate-buffered saline having a pH of 7.0 and dialyzed to a final concentration of $1 \times 10^9$ cells per ml. The resulting cell suspension was inactivated by heating at 60° C. for 30 minutes and stored at 4° C.

Equal volumes of the four strains (*S. mutans* AHT, BHT, 10449 and 6715) killed and prepared as described above, were mixed to form an antigen preparation. Each of two cows was innoculated five times at one week intervals with a five milliliter amount of this preparation at each innoculation. Commencing one month after the final innoculation, milk was collected twice daily for two weeks, freeze-dried and used in the experimental work described hereafter.

The level of anti-*S. mutans* antibody in defatted, dried milk from one of these cows was estimated using the following procedure. Fifty milligrams of dry milk was dissolved in one milliliter of distilled water and four sets of serial two-fold dilutions were made in saline (four tubes of ½ strength, four tubes of ¼ strength, etc.). To each set of dilution tubes was added a single strain of formalin-killed *S. mutans*, such as AHT, BHT, 10449 or 6715, at a concentration of $2 \times 10^8$ cells/ml. The tubes were shaken to allow admixture and incubated for four hours at 37° C. Endpoint agglutination titers were recorded and the tubes were reincubated to 24 hours at 4° C. at which time endpoint titers were again recorded. As a result of these duplicate titrations, the following results were obtained:

| Antigen Employed | Immune Bovine Milk Titer |
| --- | --- |
| *S. mutans* AHT | 64 |
| *S. mutans* BHT | 1024 |
| *S. mutans* 10449 | <2 |
| *S. mutans* 6715 | 256 |
| *S. sanguis* | 0 |

As can be seen, three of the four strains showed significant agglutinin titers, however no antibodies to *S. mutans* 10449 could be detected. For this reason, the experimental animals were infected with only virulent *S. mutans* AHT, BHT and 6715 and not with *S. mutans* 10449. No detectable antibodies could be detected to another oral bacterial strain, *Streptococcus sanguis*, against which the cows had not been immunized and which was used as a control.

The anti-*Streptococcus mutans* antibody in the immune bovine milk produced according to the preceding procedure was tested using young gnotobiotic rats.

Pregnant gnotobiotic rat dams (COBS/CD strain), obtained from Charles River Laboratories (Wilmington, Mass.), were used as the source of the young gnotobiotic rats. Each dam was maintained in a sterile cage and provided with sterile water and a special defined diet containing antibiotics in order to suppress the bacterial flora. On delivery, each litter of rat pups was reduced to 9 pups per dam. The litters were divided into three groups (Groups A, B and C), each group containing 5 litters with 9 pups per litter, or a total of 45 pups per group. At 19 days of age, the rat pups were weaned into sterile cages and fed the following completely defined, caries-promoting diet until they were 45 days of age:

| Components | Amount (percent by weight) |
| --- | --- |
| Sucrose (6× pulverized) | 5.0 |
| Lactalbumin (milk protein) | 20.0 |
| Salt mixture (MIT) | 3.0 |
| Vitamin mixture | 1.0 |
| Cottenseed oil | 3.0 |
| Cellulose | 6.0 |
| Cornstarch | 62.0 |
| Total | 100.0 |

Dry milk was used as the lactalbumin source. Analysis of both immune and non-immune dry milk indicates that it contains approximately 29% lactalbumin (milk protein) so that 690 grams of dry milk (either immune or non-immune) was required to obtain a lactalbumin content of 200 grams. Therefore, the composition of the diet, by weight, is as follows:

| Components | Amount (grams) |
| --- | --- |
| Sucrose | 50 |
| Dry Milk | 690 |
| Salt mixture (MIT) | 30 |
| Vitamin mixture | 10 |
| Cottonseed oil | 30 |
| Cellulose | 60 |
| Cornstarch | 620 |
| Total | 1,490 |

Group A rat pups received this diet using the immune bovine milk as the lactalbumin source while groups B and C received the diet using non-immune bovine milk (from a commercial source) as the lactalbumin source.

At the 25th day of age, each rat in group A (immune milk diet) and group B (non-immune milk diet) were challenged, or infected, with *S. mutans* AHT, BHT and 6715 by introducing swabs of each culture into the oral cavity of each rat. Eighteen hour cultures of *S. mutans* AHT, BHT and 6715 were used. Group C (non-immune milk diet) was not challenged and acted as a control. At the 26th day of age and again at the 27th day, oral swabs were obtained from three of four rats from each litter in groups A and B and plated on blood and Mitissalivarius agar to confirm colonization of *S. mutans* AHT, BHT and 6715 in the oral cavities of the rats in groups A and B. In every instance *S. mutans* AHT, BHT and 6715 were reisolated. Additional swabs taken in certain animals at sacrifice also showed positive cultures of *S. mutans* AHT, BHT and 6715 indicating continued colonization.

At the 45th day of age, the rats were weighed and then sacrificed by decapitation with a guillotine. The heads were autoclaved for 5 minutes to loosen the soft tissue and the mandibles were then dissected, cleaned and stained with 0.4% murexide to 70% alcohol. After staining, the molars were hemisectioned with a dental drill and carious lesions scored by the Keyes procedure described in Keyes P. J., *Dental Research*, vol. 37, p. 1077 (1958). A total of 15 rats from each group were analyzed in this manner. The scores from each group of rats were statistically reduced by computing their means, standard deviations and standard errors. Differences among means were evaluated by analysis of variances and multiple mean comparisons with the Duncan test.

The results of caries scores from the 15 rats analyzed in each group are expressed in the following table:

| Group | Mean Caries Scores[a] Enamel | Dentin | Mean Body Weights (grams) |
| --- | --- | --- | --- |
| A (Immune Milk, Infected) | 1.8 ± 0.5 (17%)[b] | 0.5 ± 0.2 (8%) | 116 |
| B (Non-Immune Milk, Infected) | 10.8 ± 0.7 (100%) | 6.2 ± 0.8 (100%) | 110 |
| C (Non-Immune Milk, Non Infected) | 0.9 ± 0.5 (8%) | 0.1 ± 0.1 (2%) | 114 |

[a]Evaluated by the Keyes procedure. Scores ± standard error. Groups A and C are significantly different from Group B. ($p \leq 0.001$). Groups A and C are not significantly different.
[b]Caries scores observed in Groups A and C expressed as percent observed in Group B.

From this data it is apparent that the bovine milk immunoglobulin generated as described in this example does contain antibodies to *Streptococcus mutans* and that these antibodies, when brought in contact with teeth render the colonization of *Streptococcus mutans* inert, thereby inhibiting tooth decay.

Based on animal tests and some human testing a therapeutically effective dosage of the dental caries immune milk, when administered as a mouthwash or toothpowder, is 1/10 of 1 gram of immune milk immunoglobulin per day having a minimum antibody titer of 1 to 1,000. Antibody titer against a specific antigen is commonly expressed as the dilution of the antiserum, in this case, immune milk, which reacts with a standard quantity of the antigen, *Streptococcus mutans*, to cause a predictable result. For example, according to the preferred dosage, 1 cc of dental caries immune milk diluted 1,000 times should contain sufficient antibody against *Streptococcus mutans* to cause the agglutination of $2 \times 10^8$ *Streptococcus mutans* cells.

While a preferred embodiment of the invention has been described, variations of the discovery will occur to those skilled in the art and these variations are intended to be covered in the following claims:

I claim:

1. The method of reducing the incidence of dental caries in animals, which includes the steps of passing into the oral cavity of the host a bovine milk immunoglobulin comprising antibodies specific to killed *Streptococcus mutans* cells in a pharmaceutically accepted vehicle.

2. The method of claim 1 wherein the antibodies are generated exogenously.

3. The method of reducing the incidence of dental caries in animals which include passive immunization by means of a therapeutically effective amount of bovine milk immunoglobulin containing antibodies specific to killed *Streptococcus mutans* cells.

4. The method of claim 3 wherein the antibodies are obtained from an exogenous source.

5. An antibody for reducing the incidence of dental caries in animals, produced by first preparing a vaccine from killed *Streptococcus mutans* bacteria, injecting said vaccine intramuscularly in healthy pregnant cows beginning three to four weeks prior to the predicted day of parturition, once a week for four weeks, and thereafter at fifteen day intervals throughout the period of lactation, collecting the milk from the immunized cows beginning the fourth week, and testing for titer to insure that the titer against *Streptococcus mutans* has reached its highest level.

6. The antibody of claim 5 incorporated in a dentifrice.

7. The antibody of claim 5 incorporated in a mouthwash.

* * * * *